(12) United States Patent
Robbins

(10) Patent No.: US 6,461,589 B2
(45) Date of Patent: *Oct. 8, 2002

(54) STANDARDIZED COMPOSITIONS WHICH FACILITATE SWALLOWING IN DYSPHAGIC SUBJECTS

(75) Inventor: Jo Anne Robbins, Madison, WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/442,704

(22) Filed: Nov. 18, 1999

(65) Prior Publication Data

US 2001/0036439 A1 Nov. 1, 2001

Related U.S. Application Data

(60) Provisional application No. 60/151,213, filed on Aug. 27, 1999.

(51) Int. Cl.$^7$ ............................................. A61K 49/04
(52) U.S. Cl. .................. 424/9.41; 424/9.4; 424/9.1; 424/1.11
(58) Field of Search ................. 424/9.4, 9.41, 424/9.411, 400, 439, 9.3, 9.1, 1.11; 206/223, 569, 570

(56) References Cited

U.S. PATENT DOCUMENTS

| | | |
|---|---|---|
| 4,020,152 A | 4/1977 | Heitz |
| 5,932,235 A | 8/1999 | Ninomiya et al. |
| 5,976,084 A | 11/1999 | Tymchuck |

OTHER PUBLICATIONS

Grawemeyer, E.A. and Pfund, M.C. (1943) "Line spread as an objective test of consistency," *Food Research*, 8:105–108.

Chen et al. Oropharynx in Patients with Cerebrovascular Disease: Evaluation with Videofluoroscopy, *Radiology*, 1990, vol. 176, pp. 641–643.

Chen et al., Clinical and Videofluoroscopic Evaluation of Swallowing in 41 Patients with Neurologic Disease, *Gastrointest. Radiol.*, 1992, vol. 17, pp. 95–98.

Li et al., Viscosity Measurements of Barium Sulfate Mixtures for Use in Motility Studies of the Pharynx and Esophagus, 1992 vol. 7, pp. 17–30.

Ott et al., Modified Barium Swallow: Clinical and Radiographic Correlation and Relation to Feeding Recommendations, *Dysphagia*, 1996, vol. 11, pp. 187–190.

Pokieser et al., Videokinematographie des Schlikaktes, *Radiologe*, 1995, vol. 35, pp. 703–711.

Stachler et al., Swallowing of Bolus Types of Postsurgical Head and Neck Cancer Patients, *Head & Neck*, Sep./Oct. 1994, pp. 413–419.

*Primary Examiner*—Dameron L. Jones
(74) *Attorney, Agent, or Firm*—Joseph T. Leone, Esq.; DeWitt Ross & Stevens, S.C.

(57) ABSTRACT

Disclosed are a viscosity-standardized combination of solutions and a method of using the solutions for the diagnosis of dysphagia and for radiographic imaging of the oropharynx.

11 Claims, No Drawings

STANDARDIZED COMPOSITIONS WHICH FACILITATE SWALLOWING IN DYSPHAGIC SUBJECTS

Priority is hereby claimed to provisional application Ser. No. 60/151,213, filed Aug. 27, 1999, the contents of which are incorporated herein by reference.

REFERENCE TO GOVERNMENT GRANT

This invention was made with United States Government support awarded by the NIH, Grant No. DC03206. The United States Government has certain rights in this invention.

FIELD OF THE INVENTION

The invention is directed to standardized, viscosity-modified, edible formulations for use with dysphagic patients and methods to gauge the viscosity of modified foods using the standardized formulations. The formulations described herein can so combined with a radio-opaque agent to facilitate improved dynamic fluoroscopic imaging of the oropharynx, hypopharynx, etc.

BACKGROUND OF THE INVENTION

The oropharyngeal physiology involved in a normal swallow is an exceedingly complex series of coordinated actions. A host of very different medical conditions, both physical and neurological in nature, can alter normal swallowing. For example, patients suffering stroke, Alzheimer's disease, amyotrophic lateral sclerosis, or traumatic brain injury can exhibit abnormal swallowing. In many instances, the abnormal swallow can and does cause aspiration of food material, both liquids and solids, into the lungs. This is especially prevalent (and life-threatening) in bed-ridden patients. Aspiration of foreign material into the airways leads to increased morbidity in hospitalized patients and can lead to pneumonia. Abnormalities in the human swallow, whether or not the condition results in aspiration of foods, is called dysphagia.

A normal human swallow can be separated into four semi-distinct phases: 1) oral preparation; 2) the oral phase; 3) the pharyngeal phase; and 4) the esophageal phase. Patients who have suffered a stroke, traumatic brain injury, or neuromuscular disorder (such as MS or ALS) have an increased risk of aspiration, and may have difficulty with either the oral phase, the pharyngeal phase or both. For instance, weak and/or uncoordinated muscle movement when chewing or in the initial oral phase of swallowing can cause food to fall into the pharynx and into the open airway before the completion of the oral phase. Or impaired propulsion can result in residue in the oral cavity, valleculae, or pharynx after the swallow, when the residue may be inhaled into the trachea. Or a delay in the onset of the pharyngeal swallowing response can result in food falling into the airway during the delay when the airway is open. Or reduced peristalsis in the pharynx can leave residue in the pharynx after the swallow is completed that can fall or be inhaled into the airway. Additionally, laryngeal or cricopharyngeal dysfunction can also lead to aspiration because of decreased closure of the airway during swallowing. Any of these conditions, or a combination of these conditions, can lead to aspiration of food into the airways.

To detect and evaluate patients who have dysphagia or are at risk of developing dysphagia, speech pathologists currently employ a roughly standard procedure for initially evaluating a patient's swallow. A bedside swallow exam performed by most speech pathologists first evaluates the patient's medical history, respiratory status, level of responsiveness, and level of cognitive impairment, if any. Evaluating swallowing can be especially difficult in patients with moderate to advanced cognitive impairment due to the inability of the patient to understand and to follow instructions.

A physical examination of the oropharynx is then performed. The muscles involved in mastication, the lips, the tongue, and the palate are examined. The position of the patient when tested (prone, seated, standing) is noted as this can have a profound effect on the swallowing mechanism. The patient's empty mouth ("dry") is evaluated. The patient is then asked to swallow one or more thin liquids, thick liquids, pureed textured, and/or solid textured foods to evaluate the swallow mechanism. In particular, the speech pathologist looks for a host of telltale signs of dysphagia such as gurgling, impaired vocal quality post-swallow, coughing, nasal regurgitation, and multiple swallows, as well as any visible signs that may indicate risk for aspiration.

While the standard bedside swallow exam to screen patients is beneficial for evaluating patients at risk for dysphagia, it sheds very little light on the whether the patient is actually aspirating and even less light on where in the swallow cycle the defect arises. Many patients, due to concomitant neurological defects, will silently aspirate, giving no indication during the bedside exam as to their condition. Aspiration in dysphagic patients, however, can be detected using a modified barium swallow fluoroscopic examination. Videofluoroscopy of the swallow mechanism is performed regularly to elucidate more clearly the anatomical or neurological deficit causing the dysphagia.

Dynamic fluoroscopic evaluation of the swallow, however, is not without its attendant difficulties and shortcomings. For instance, the imaging compositions conventionally used for fluorscopic exams are thick suspensions of barium sulfate. Barium is employed because of its large X-ray absorption cross-section, which makes it radio-opaque. The use of barium sulfate suspensions as a radiological contrast medium has a number of drawbacks. A first drawback is that conventional barium sulfate suspensions generally have either poor adhesion to the walls of the oropharynx or too much adhesion. These compositions, having been initially designed to image the gastrointestinal tract, have not been altered much if any, for use in imaging the mouth and throat. If the walls of the oropharyngeal tract are not sufficiently coated with the contrast agent, an X-ray image cannot be generated; there simply isn't enough contrast to visualize the relevant structures. Conversely, if the suspension is made thicker to encourage adhesion, the thick, chalky suspension actually coats the mouth and throat and physically alters the movement of the muscles used for swallowing. Consequently, the image generated is not necessarily indicative of the true swallow response exhibited by the patient. Further, total clearance of material from the oropharyngeal and esophageal cavities would be a useful visual cue to determine whether the function of these structures is within normal limits. If the oropharynx is coated with too much contrast agent, the dense X-ray cross-section creates a complete opacity in the resultant X-ray exposure, which does not provide sufficient detail of the structures involved in swallowing. A complicating factor is the taste and chalky texture of barium suspensions, which makes them generally unpleasant to hold in the mouth and to swallow. Substances that are more food-like in taste and texture would more likely elicit a more representative swallow response.

See, for example, U.S. Pat. No. 4,020,152 to Heitz, which describes barium titanate and barium zirconate X-ray contrast agents. This patent specifically notes that it is quite difficult to generate fluoroscopic images of the oropharyngeal cavity. Heitz states that patients have great difficulty in holding a mouthful of contrast medium at the very back of their throats for a long time without swallowing. When the patient swallows the barium sulfate suspension, it slides over the mucous membranes, often without leaving sufficient contrast agent in place to generate an image. Heitz believes the lack of adhesion is due to the saliva covering the walls of the oropharynx, which substantially reduces the adherence of a barium sulfate suspension. As a result, radiological examination of this key physiological intersection, the junction where aspiration occurs, is difficult and often leads to only mediocre imaging. Failure to generate a clean radiological image of the swallow leads to imprecise diagnosis and treatment.

Moreover, once a patient has been diagnosed as having dysphagia and is known to be aspirating foods, some compensatory treatment must be implemented to prevent further aspiration. One method widely employed is to alter the consistency (i.e., the viscosity) of liquid foods. Thickened liquid foods are thought to inhibit aspiration by providing greater mechanical resistance to the muscles involved in swallowing and providing greater "mouthfeel" to the patient. See, for example, U.S. Pat. No. 5,932,235, to Ninomiya et al.: This patent describes a jellied preparation containing carrageenan, locust bean gum, and a polyacrylic acid. The preparation can be used to thicken liquid foodstuffs.

In hospital, nursing home, and clinical settings, thickened liquids deemed to be "nectar thick" or the more viscous "honey thick" are used to feed dysphagic patients. For instance, preferred liquid foods such as milk, coffee, or tea are thickened with an added thickening agent prior to being fed to a dysphagic subject. However, there has not been implemented any objective set of criteria to define the levels of thickness/viscosity which constitute a nectar thick composition versus a honey thick composition. The health provider simply thickens the desired food to a subjective thickness and provides it to the patient. This lack of standardization fosters great variability in practice. In short, individual speech pathologists, dieticians, food service managers, and food manufacturers arbitrarily determine, based upon their own subjective evaluation, what constitutes a nectar thick composition and a honey thick composition. In the vast majority of instances, no objective measurement of the increased viscosity of the modified food is taken. If a measurement is taken, it is done using rough, empirical evaluations of viscosity, such as the Line Spreading Test (LST), a test developed in the 1940s to gauge the consistency of foods. See Grawemeyer, E. A. and Pfund, M. C. (1943) "Line spread as an objective test of consistency," *Food Research* 8:105–108. This greatly hinders gathering detailed information on the efficacy of using thickened liquids in the treatment of dysphagia.

Therefore, there continues to be a long-felt and unmet need in the study of dysphagia for a viscosity-standardized set of edible compositions for both the gross evaluation of dysphagia and for a corresponding viscosity-standardized set of edible compositions containing a radio-opaque agent for use in the radiographic imaging of the mouth and throat.

SUMMARY OF THE INVENTION

A first embodiment of the invention is directed to a standardized combination of edible solutions for evaluating human subjects for the presence of dysphagia. Because the solutions have a standard and known viscosity, they promote the systematic study and treatment of swallowing disorders. The combination comprises three solutions: the first a "thin" composition, the second a "nectar thick" composition and the third a "honey thick" composition. The first edible composition has a known viscosity of less than about 30 cp. The second edible composition has a known viscosity of between about 150 cp and about 350 cp at about 23° C.; while the third edible composition has a known viscosity of between about 2,000 cp and about 4,000 cp at about 23° C. These latter compositions are a good deal more viscous than thin liquids such as water or coffee (which have a viscosity of about 10 cp), which are simulated by the first composition.

A second embodiment of the invention is an improvement which utilizes the standardized solutions to improve radiographic imaging of the mouth and throat. Specifically, in a composition for radiographic imaging of swallowing in humans, wherein the composition comprises a vehicle and a radio-opaque imaging agent, the improvement which is the subject of the present invention is a standardized combination of edible solutions of defined viscosity as noted above. These compositions include a radio-opaque imaging agent, such as barium sulfate.

A third embodiment of the invention is drawn to a method for evaluating a human subject for dysphagia. The method comprises providing a standardized combination of edible solutions as described hereinabove. A patient's swallowing ability is then evaluated for indications of dysphagia when the subject swallows the first edible composition. The patient's swallowing ability is then evaluated for indications of dysphagia when the subject swallows the second and third edible composition. Because the compositions are of known and standardized viscosity, far more useful information is generated regarding the swallowing defects exhibited by the patient.

The utilities of the subject compositions and methods are several-fold. A primary utility is that by using standardized compositions, consistency in treating dysphagia is promoted. Rather than supplying patients an arbitrarily thickened food or X-ray imaging product, the patient is supplied a composition of known viscosity. The patient's ability to swallow the composition properly is then evaluated, either by a gross physical exam or radiographic means or other visualization means, including X-ray, magnetic resonance imaging, and the like. Using three standard solutions allows the results of three distinct swallowing studies (one using the nectar-thick composition, the other using the honey-thick composition) to be compared and contrasted. Moreover, it allows the results from different patients to be compared directly, without variations in viscosity of the imaging agent introducing uncontrolled variables into the comparison.

The compositions are useful in radiographic imaging of the mouth because they taste more food-like than conventional barium-containing imaging agents and are therefore more palatable. The specific viscosities recited herein for the compositions also promotes the proper amount of adhesion between the composition and the mucus membranes lining the mouth and throat. Consequently, the compositions deposit sufficient imaging material on the mucus membranes to generate a radiographic image, but not so much imaging material as to change the swallowing dynamics of the patient under study, nor leave an artificial coating after swallowing is complete. This is a distinct improvement over conventional barium agents, whose thick, chalky consistency is neither palatable, nor conducive to the generation of good radiographic images of the throat and mouth.

DETAILED DESCRIPTION

The first embodiment of the invention is a series of standardized solutions for evaluating dysphagia in human subjects. Specifically, three solutions are required: a water-like "thin" composition having a viscosity less than about 30 cp, a nectar-thick composition having a viscosity of between about 150 and 350 cp and a honey-thick composition having a viscosity of between about 2,000 cp and about 4,000 cp. More preferable is that the viscosity of the nectar-thick composition ranges between about 200 cp and about 300 cp and the viscosity of the honey-thick composition ranges between about 2,500 cp and about 3,500 cp. More preferably still is that the nectar-thick composition has a viscosity of about 270 cp and the honey-thick composition has a viscosity of about 2,800 cp.

Viscosity of the compositions is measured at room temperature, generally about 23° C., and can be determined using any number of conventional and commercially available spindle-type viscometers, such as those manufactured by Brookfield Engineering Laboratories, Middleboro, Mass. Brookfield's instruments use a rotating spindle immersed in the fluid to measure viscosity. The preferred instrument from among Brookfield's offerings is Model LVDV1+, an 18-speed model with digital readout. Viscometers and their operation are widely known and will not be described herein.

For radiographic imaging of the mouth and throat, it is preferred that compositions having the above-noted viscosities are formulated using apple juice as a base vehicle. Apple juice is very advantageous for this purpose because it is widely available, relatively inexpensive, pulp-free, is quite palatable and familiar to virtually everyone, and can be stored and transported as a concentrate. To the apple juice vehicle is added a thickening agent and/or a radio-opaque imaging agent. Because a suspension of radio-opaque material will, by itself, increase the viscosity of a thin liquid to within the above-noted viscosities, depending upon the nature of the suspension used, a thickening agent may not be required to arrive at a thin, nectar-thick, or honey-thick composition.

Any other type of non-pulpy juice, liquid, or water may be used as the vehicle. A fruit juice is much preferred as the vehicle, however, because of its familiar taste and aroma. An ultimate goal of the invention being an accurate evaluation of the patient's true swallowing dynamics, presenting an imaging composition which is as closely simulative as possible to a food the patient would normally ingest and enjoy is highly desirable.

The preferred thickening agent for use in the present invention is a commercially available preparation marketed by Novartis (Basel, Switzerland) under the registered trademark "THICKENUP." While the "THICKENUP" formulation is preferred, any suitable food thickener (e.g., "THICK IT"-brand thickener (Milanti Co.) starch, sugars, glycols, etc., may be used).

The preferred radio-opaque imaging agent is a suspension of barium sulfate. Suitable barium sulfate and barium sulfate suspensions are available commercially from numerous sources. Preferred commercially available barium sulfate and edible suspensions thereof can be had from the E-Z-EM Corporation, Westbury, N.Y. Specifically preferred are the products bearing E-Z-EM catalog nos. L147, L164, L168, and L178 (liquid barium sulfate suspensions), catalog no. 764 (high density barium sulfate suspension), and catalog no. 745 (bulk barium sulfate for suspension). Particularly preferred for use in the nectar-thick and honey-thick solutions of the present invention is "EnteroH" brand barium suspension (catalog no. L147), from E-Z-EM. For the thin standard, "Liquid Polibar" brand barium suspension (catalog no. L164) is preferred.

It is critical when formulating the compositions to include the proper amount of imaging agent and/or thickener because both components will contribute to the ultimate viscosity of the composition and there must also be the proper amount of imaging agent present in the composition to generate useful radiographic images. If there is too little imaging agent, the composition will be invisible to X-rays, if there is too much imaging agent, the composition will be too opaque.

For the thin composition, the preferred formulation is as follows:

Commercially purchased apple juice at room temperature, (single-strength, about 6.5 to 7.0 brix, at about 23° C.), 140 mL, is admixed with 90 mL of "Entero H" brand barium sulfate suspension, available commercially from E-Z-EM. The mixture is thoroughly agitated until uniform. To ensure consistency of application, it is much preferred that the composition be made no more than 2.5 hours before use. The formulation should be administered at room temperature. This formulation yields a low-viscosity composition of about 25 cp.

For the nectar-thick composition, the preferred formulation is as follows:

Commercially purchased apple juice at room temperature, (single-strength, about 6.5 to 7.0 brix, at about 23° C.), 30 mL, is admixed with 150 mL of "Liquid Polibar" brand barium sulfate suspension, available commercially from E-Z-EM corporation. The mixture is thoroughly agitated until uniform. To ensure consistency of application, it is much preferred that the composition be made no more than 2.5 hours before use. The formulation should be administered at room temperature.

To test the variability of the viscosity of the nectar-thick formulation made according to the above recipe, eight (8) separate nectar-thick sample batches were made using commercially available apple juice and "EnteroH" brand barium sulfate suspension and the viscosity of the eight samples evaluated. For this population of batch formulations (n=8), the viscosity study showed a mean viscosity of 267.75 cp, with a standard deviation of 14.93 cp. The lowest viscosity recorded for a single sample in this study was 233 cp, and the highest viscosity for a single sample was 278 cp (a range of 45 cp).

For the honey-thick composition, the preferred formulation is as follows:

Commercially purchased apple juice at room temperature, (single-strength, about 6.5 to 7.0 brix, at about 23° C.), 120 mL, is admixed with 34.53 cubic centimeters (2.5 tablespoons) of "THICKENUP" brand thickener. (As sold commercially, the "THICKENUP" thickener includes a sliding measuring spoon.) The juice and thickener mixture is agitated thoroughly and allowed to sit undisturbed for no less than 10 minutes. To this mixture is added 92 mL of "Liquid Polibar" brand barium sulfate suspension, available commercially from E-Z-EM Corporation. The mixture is again thoroughly agitated until uniform. To ensure consistency of application, it is much preferred that the composition be made no more than 2.5 hours before use. The formulation should be administered at room temperature.

In testing the variability of the viscosity of formulations made according to the above recipe for honey-thick compositions, eight (8) separate honey-thick sample batches were made using commercially available apple juice and Component A and the viscosity of the eight samples evaluated. For this population of batch formulations (n=8), the viscosity study showed a mean viscosity of 2,816.33 cp, with a standard deviation of 103.26 cp. The lowest viscosity recorded for a single sample in this study was 2759 cp, and the highest viscosity for a single sample was 3015 cp (a range of 256 cp).

For radiographic imaging purposes, the patient is positioned laterally before a suitable fluoroscopic device and asked to swallow one or more of the three compositions. A videofluoroscope and suitable recording equipment are then used to visualize and record the passage of the composition through the mouth and throat during and after swallowing. If desired, the study can be performed using any combination or all three of the compositions.

What is claimed is:

1. A kit of individual viscosity-standardized edible solutions for evaluating human subjects for dysphagia, the kit comprising:
   a. a first edible solution having a known viscosity of less than about 30 cp at about 23° C. disposed in a first container;
   b. a second edible solution having a known viscosity of between about 150 cp and about 350 cp at about 23° C. disposed in a second container; and
   c. a third edible solution having a known viscosity of between about 2,000 cp and about 4,000 cp at about 23° C. disposed in a third container.

2. The kit according to claim 1, wherein the second edible solution has a viscosity of between about 200 cp and about 300 cp, and the third edible solution has a viscosity of between about 2,500 cp and 3,500 cp.

3. The kit according to claim 1, wherein the first edible solution has a viscosity of about 25 cp, the second edible solution has a viscosity of about 270 cp, and the third edible solution has a viscosity of about 2,800 cp.

4. The kit according to claim 1, wherein the first, second, and third edible solutions comprise an imaging agent.

5. The kit according to claim 4, wherein the imaging agent is a radio-opaque imaging agent.

6. The kit according to claim 5, wherein the radio-opaque imaging agent is a barium-containing compound.

7. The kit according to claim 5, wherein the radio-opaque imaging agent is barium sulfate.

8. A method for evaluating a human subject for dysphagia, the method comprising:
   (a) providing:
      (i) a first edible composition having a viscosity of less than about 30 cp at 23° C.
      (ii) a second edible composition having a known viscosity of between about 150 cp and about 350 cp at about 23° C.;
      (iii) a third edible composition having a known viscosity of between about 2,000 cp and about 4,000 cp at about 23° C.; and
   (b)
      (i) evaluating swallowing in the subject for indications of dysphagia during and after the subject swallows the first edible compositions;
      (ii) evaluating swallowing in the subject for indications of dysphagia during and after the subject swallows the second edible composition; and
      (iii) evaluating swallowing in the subject for indications of dysphagia during and after the subject swallows the third edible composition.

9. The method according to claim 8, wherein in step (a) the first, second, and third edible compositions comprise a radio-opaque imaging agent that does not leave an artificial coating in the mouth and oropharynx after swallowing is complete; and in steps (b)(i), (b)(ii), and (b)(iii), swallowing is evaluated by radiography.

10. The method according to claim 8, wherein the edible composition comprises a non-pulpy fruit juice wherein viscosity of the fruit juice is modified by adding a thickening agent thereto.

11. The method according to claim 10, wherein the fruit juice is apple juice.

* * * * *